(12) United States Patent
Tokhtuev et al.

(10) Patent No.: US 8,120,500 B2
(45) Date of Patent: Feb. 21, 2012

(54) ACOUSTIC FLUID PRESENCE/ABSENCE DETECTION

(75) Inventors: Eugene Tokhtuev, Duluth, MN (US);
Christopher J. Owen, Duluth, MN (US); Anatoly Skirda, Hermantown, MN (US); Viktor Slobodyan, Duluth, MN (US); Anna Pilipchenko, Duluth, MN (US)

(73) Assignee: Ecolab Inc., St. Paul, MN (US)

( * ) Notice: Subject to any disclaimer, the term of this patent is extended or adjusted under 35 U.S.C. 154(b) by 566 days.

(21) Appl. No.: 12/329,788

(22) Filed: Dec. 8, 2008

(65) Prior Publication Data

US 2010/0141460 A1    Jun. 10, 2010

(51) Int. Cl.
*G08B 21/00* (2006.01)
*G01F 23/296* (2006.01)
(52) U.S. Cl. ........... 340/618; 340/612; 340/621; 702/55
(58) Field of Classification Search .................. 340/618, 340/603, 606, 612, 621; 73/864.73, 453, 73/53.01; 138/104; 702/55; 356/409, 436
See application file for complete search history.

(56) References Cited

U.S. PATENT DOCUMENTS

| | | |
|---|---|---|
| 3,974,681 A | 8/1976 | Namery |
| 4,068,521 A | 1/1978 | Cosentino et al. |
| 4,235,095 A | 11/1980 | Liebermann |
| 4,341,116 A | 7/1982 | Bilstad et al. |
| 4,418,565 A | 12/1983 | St. John |
| 4,565,500 A | 1/1986 | Jeensalute et al. |
| 4,668,945 A | 5/1987 | Aldrovandi et al. |
| 4,764,166 A | 8/1988 | Spani |
| 5,015,995 A | 5/1991 | Holroyd |
| 5,064,412 A | 11/1991 | Henke et al. |
| 5,123,275 A | 6/1992 | Daoud et al. |
| 5,180,287 A | 1/1993 | Natwick et al. |
| 5,191,795 A | 3/1993 | Fellingham et al. |
| 5,392,638 A | 2/1995 | Kawahara |
| 5,394,732 A | 3/1995 | Johnson et al. |
| 5,470,604 A | 11/1995 | Neoh |
| 5,507,178 A | 4/1996 | Dam |
| 5,537,853 A | 7/1996 | Finburgh et al. |
| 5,583,280 A | 12/1996 | Mo et al. |
| 5,843,035 A | 12/1998 | Bowman et al. |

(Continued)

FOREIGN PATENT DOCUMENTS

JP    2001255313 A    9/2001
(Continued)

OTHER PUBLICATIONS

Piezo Technologies, "Air-In-Line Technology Experts, Advancing Air-In-Line Applications through Innovative Piezo Materials and World-Class Engineering", Nov. 2006, (1 page).

(Continued)

*Primary Examiner* — Toan N Pham
(74) *Attorney, Agent, or Firm* — Shumaker & Sieffert, P.A.

(57) ABSTRACT

An acoustic sensor detects presence and/or absence of fluid in a fluid delivery medium. The acoustic sensor detects fluid absence based on the difference of the speed of sound between air and a fluid. For example, the acoustic sensor may detect fluid absence based on a phase shift between acoustic signals transmitted through the fluid delivery medium when fluid is present as compared to acoustic signals transmitted through the fluid delivery medium when fluid is absent, e.g., when air or bubbles are present in the fluid delivery medium.

27 Claims, 7 Drawing Sheets

U.S. PATENT DOCUMENTS

| | | | |
|---|---|---|---|
| 5,983,723 A | 11/1999 | Buckin et al. | |
| 6,119,070 A * | 9/2000 | Beneteau et al. | 702/45 |
| 6,142,008 A | 11/2000 | Cole et al. | |
| 6,186,004 B1 | 2/2001 | Kaduchak et al. | |
| 6,212,936 B1 | 4/2001 | Meisberger | |
| 6,408,679 B1 | 6/2002 | Kline-Schoder et al. | |
| 6,631,639 B1 | 10/2003 | Dam et al. | |
| 6,658,946 B2 * | 12/2003 | Lipscomb et al. | 73/861.42 |
| 6,823,715 B2 | 11/2004 | Kobayakawa et al. | |
| 6,851,453 B2 * | 2/2005 | Lipscomb et al. | 138/104 |
| 7,013,703 B2 | 3/2006 | Derek et al. | |
| 7,178,396 B2 | 2/2007 | Carkner et al. | |
| 2009/0097029 A1 * | 4/2009 | Tokhtuev et al. | 356/409 |

FOREIGN PATENT DOCUMENTS

| | | |
|---|---|---|
| JP | 2005043091 A | 2/2005 |
| JP | 2007278747 A | 10/2007 |

OTHER PUBLICATIONS

Introtek International, L.P., "AD8/AD9 Series Sensor, The AD8/AD9 ultrasonic air bubble, air-in-line and liquid level sensors invorporate Introtek's latest generation MEC pulse-type ultrasonic circuity", Jan. 2006, (2 pages).

International Search Report and Written Opinion of international application No. PCT/IB2009/055557, dated May 31, 2010, 9 pp.

* cited by examiner

ACOUSTIC FLUID PRESENCE/ABSENCE DETECTION

TECHNICAL FIELD

The present invention relates to detection of the presence and/or absence of fluid in a fluid delivery medium.

BACKGROUND

Fluid dispensing systems typically deliver quantities of fluid via tubing or pipes to one or more components within the system. In certain fields, fluid dispensing systems may deliver small quantities of fluid. For example, in the medical field, a fluid dispensing system may deliver small quantities of fluid into a patient's vascular system. In other fields, fluid dispensing systems may deliver larger quantities of fluid. For example, in a large-scale hotel, laundry or restaurant facility, a fluid dispensing system may deliver large quantities of detergent, rinse agent, bleach or other cleaning agents via tubing to a large number of commercial dishwashing or laundry machines on a continual or periodic basis.

A fluid dispensing system may include a pump and a product reservoir. The pump draws fluid from the product reservoir and delivers it to another component within the system via tubing. Many different forms of pumps may be used within a fluid dispensing system. In addition, the fluid dispensing system may include multiple different pumps within a pump assembly, or within multiple pump assemblies. Further, the fluid dispensing system may include a controller that controls operation of the one or more pumps within the system.

In medical applications, ultrasonic air or bubble detectors detect bubble or air presence in the blood stream or drip chamber systems to prevent bubble penetration to patient blood. The wavelengths used are generally of the same order as the size of the bubbles to be detected. To detect very small bubbles, high frequency sound of several megahertz (ultrasound) may be used. These devices typically include an ultrasonic piezoelectric transmitter and receiver located on opposite sides of the piping/tubing. Such systems may also include special acoustic lenses to transfer and focus the acoustic energy to the examined area.

These systems use a change in signal amplitude of the received signal as compared to the transmitted signal as the criterion for detection of bubble presence. Generally, the amplitude of the detected signal decreases if bubbles are present or the fluid level is down due to defocusing of acoustic energy.

SUMMARY

In general, the invention relates to detection of the presence and/or absence of fluid in a fluid delivery medium, or detection of a drop of fluid below a predetermined level, using acoustic techniques. The invention detects absence of fluid based on the difference in the speed of sound between air and water (or other fluid). For example, the invention may detect fluid absence based on a phase shift in electronic signals detected with fluid presence vs. fluid absence (e.g., the presence of air or bubbles) in the fluid delivery medium. The invention may detect absence and/or presence of a variety of fluids having differing color, transparency or turbidity.

Fluid absence detection may be used to determine when a fluid product in a fluid dispensing system is empty or approaching empty. For example, in a fluid dispensing system in which one or more products are delivered to one or more dispensing points, one or more sensors may be utilized to detect presence or absence of product within one or more fluid delivery mediums. The sensor(s) may detect presence or absence of product in the fluid delivery medium and may provide an out-of-product alert when product absence is determined, to alert a user or service technician that the product needs to be refilled or replaced.

In one embodiment, the invention is directed to a method comprising generating an excitation signal having an excitation frequency, emitting, in response to the excitation signal, an acoustic interrogation signal having the excitation frequency into a fluid delivery medium in which presence or absence of a fluid is to be determined, receiving the acoustic interrogation signal transmitted through the fluid delivery medium and generating therefrom an acoustic signal output, determining a phase shift between the acoustic signal output and the excitation signal, and determining presence or absence of the fluid within the fluid delivery medium based on the phase shift.

In another embodiment, the invention is directed to a sensor, comprising an acoustic transmitter, driven by an excitation signal having an excitation frequency, that emits an acoustic interrogation signal having the excitation frequency into a fluid delivery medium in which presence or absence of a fluid is to be determined, an acoustic detector that generates an acoustic signal output having the excitation frequency based on detection of the acoustic interrogation signal transmitted through the fluid delivery medium, and a controller that calculates a phase shift between the acoustic signal output and the excitation signal, compares the phase shift with at least one predetermined threshold criteria and determines presence or absence of the fluid within the fluid delivery medium based on the phase shift.

In another embodiment, the invention is directed to a computer readable medium comprising instructions that cause a programmable processor to generate an excitation signal that excites emission of an acoustic interrogation signal into a fluid delivery medium in which presence or absence of a fluid is to be determined, receive the acoustic interrogation signal transmitted through the fluid delivery medium and generate therefrom an acoustic signal output, determine a phase shift between the acoustic signal output and the excitation signal, and determine presence or absence of the fluid within the fluid delivery medium based on the phase shift.

The details of one or more embodiments of the invention are set forth in the accompanying drawings and the description below. Other features, objects, and advantages of the invention will be apparent from the description and drawings, and from the claims.

DETAILED DESCRIPTION

In general, the invention relates to detection of fluid presence and/or absence in a fluid delivery medium. The invention detects fluid absence using the difference in speed of sound between air and a fluid. For example, the acoustic sensor may detect fluid absence based on a phase shift between acoustic signals transmitted through the fluid delivery medium when fluid is present as compared to acoustic signals transmitted through the fluid delivery medium when fluid is absent, e.g., when air or bubbles are present in the fluid delivery medium.

The present invention may provide a fluid presence and/or absence detection that is appropriate for a wide variety of fluids (e.g., varying in viscosity, optical transparency, color, turbidity, etc.) and different types of fluid delivery mediums (e.g., varying in diameter, optical transparency, opacity, presence of braiding or mesh, etc.).

Figure 1A:
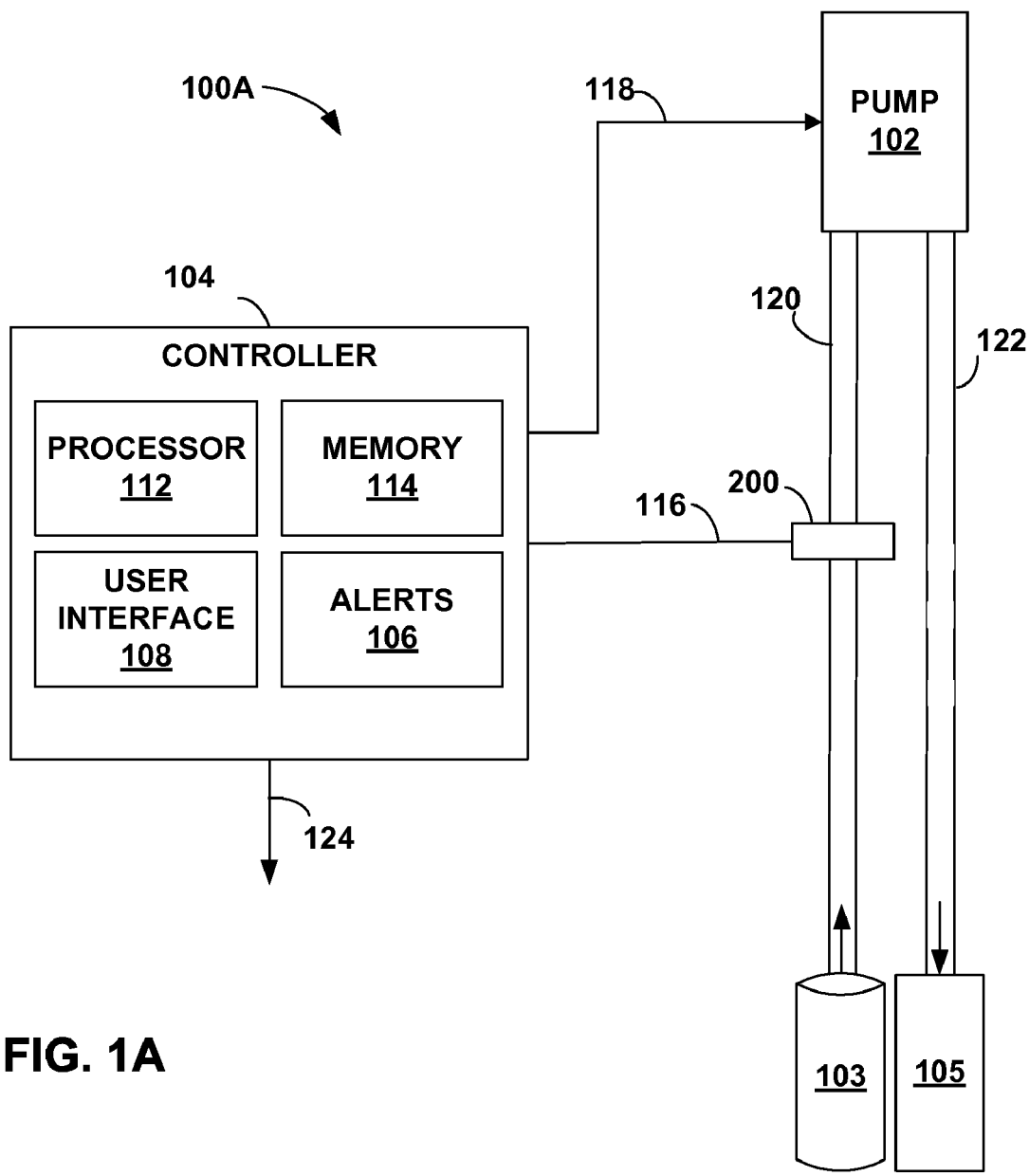
FIG. 1A is a block diagram illustrating an example of a fluid dispensing system utilizing an acoustic sensor that detects presence and/or absence of a product to be dispensed.

FIG. 1A is a diagram illustrating an example fluid dispensing system 100A and an acoustic sensor 200 that detects presence and/or absence of a product to be dispensed. Fluid dispensing system 100A includes a system controller 104, a pump 102 and a product reservoir 103. Pump 102 draws the product from reservoir 103 under control of system controller 104 and delivers the product to a dispensing site 105. Pump 102 draws product from product reservoir 103 through an input fluid delivery medium 120 and supplies fluid to dispensing site 105 via an output fluid delivery medium 122. Product reservoir 103 may contain any one of a multitude of different types of fluid products having varying degrees of color, transparency and/or turbidity.

Controller 104 may include a processor 112, a user interface 108, a memory 114 and alerts 106. Controller 104 communicates with pump 102 via a connection 118. Depending upon the application, controller 104 may communicate with dispensing site 105 via another connection (not shown). Signals generated by acoustic sensor 200 are communicated to controller 104 via connection 116. Connection 116 may include, for example, a standard I2C connection. However, any appropriate wired or wireless connection/communication channel known in the art may be used. Controller 104 may further include at least one external connection 124 such as an internet, telephone, wireless or other connection for achieving external communication.

Memory 114 stores software for running system controller 104 and also stores data that is generated or used by processor 112. Processor 112 runs software stored in memory 114 to manage operation of system 104. User interface 108 may be as simple as a few user actuatable buttons or may include a display, a keyboard or keypad, mouse or other appropriate mechanisms for communicating with a user.

Dispensing site 105 may be an end use location of the product or may be some other intermediate location. For example, when fluid dispensing system 100A is used in a commercial laundry or kitchen application, dispensing site 105 may be a washing machine or dish machine, in which case the product(s) may be dispensed into an on-unit dispense mechanism or directly into the wash environment. In that example, the product(s) dispensed may include laundry or dish detergent, fabric softener, bleach, sanitizer, rinse agent, etc. As another example, when fluid dispensing system is used in a hotel, business, industrial or other application in which service employees perform cleaning duties, dispensing site 105 may be a bucket, pail or other vessel into which the product(s) are dispensed. Dispensing site 105 may also be a hose or other tubing from which the fluid(s) is directed to a desired location. It shall be understood that fluid dispensing system 100 may be used in many different applications in which fluid is dispensed and that the invention is not limited in this respect. Examples of applications in which fluid dispensing system 100 may be used include laundry applications, dishwashing applications, commercial cleaning operations, food preparation and packaging applications, industrial processes, and many other applications known in the art.

Input fluid delivery medium 120 and output fluid delivery medium 122 may be implemented using any type of flexible or inflexible fluid delivery medium, depending upon the application. Fluid delivery mediums 120/122 may include tubing, a pipeline, or other suitable medium for the delivery of fluid. The fluid delivery medium(s) may be transparent, translucent, braided or other type of tubing. For simplicity and not by limitation, input fluid delivery medium 120 and output fluid delivery medium 122 will be referred to herein as "input tubing 120" and "output tubing 122," respectively. Input tubing 120, output tubing 122 and pump 102 may be referred to herein as a "dispensing channel."

Pump 102 may be any form of pumping mechanism that supplies fluid from product reservoir 103 to dispensing site 105. For example, pump 102 may comprise a peristaltic pump or other form of continuous pump, a positive-displacement pump or other type of pump appropriate for the particular application.

In the example system shown in FIG. 1A, acoustic sensor 200 is positioned to detect presence and/or absence of product within input tubing 120. It shall be understood, however, that acoustic sensor could be otherwise positioned. For example, acoustic sensor 200 could be positioned elsewhere along input tubing 120 or anywhere along output tubing 122.

In operation, when fluid dispensing system 100A attempts a dispensing cycle from a product reservoir 103 that has product remaining, pump 102 draws fluid from product reservoir via input tubing 120 and delivers it to dispensing site 105 via output tubing 122. Thus, when product is present in product reservoir 103, input tubing 120 will likewise contain product during a dispensing cycle. Over time, as operation continues and more and more product is dispensed, the amount of product remaining in product reservoir 103 decreases until it becomes substantially empty. Because product is no longer available to dispense, pump 102 is unable to draw product out of product reservoir 103 and into input tubing 120. As a result, a relatively larger amount of air (as compared to product) is drawn into input tubing 120.

Acoustic sensor 200 obtains acoustic information concerning presence and/or absence of product within input tubing 120. When acoustic sensor 200 detects that the acoustic information satisfies predetermined out-of-product threshold criteria, acoustic sensor 200 detects an absence of fluid within input tubing 200.

For purposes of the present description, an "out-of-product event" is defined as an event in which acoustic sensor 200 detects an absence of fluid within input tubing 200 that satisfies the predetermined out-of-product threshold criteria. When acoustic sensor 200 detects an out-of-product event, acoustic sensor 200 may generate an out-of-product alert. The out-of-product alert may take the form of an out-of-product message to system controller 104. In response to the out-of-product message received from acoustic sensor 200, controller 104 may generate a visual and/or audible out-of-product alert 106, such as an indicator LED, or text/graphics with or without accompanying sound, etc., displayed on user interface 108. Alternatively or in addition, controller 104 may initiate and send an out-of-product message (such as via pager, e-mail, cell phone, text message, or other form of electronic communication, etc.) to a technical service provider via external connection 124.

When an out-of-product event is detected, a user (such as an employee or service technician) may manually refill or replace product reservoir 103. In this embodiment, the user may temporarily halt or shutdown operation of system 100A before refilling or replacing product reservoir 103. The user may manually do this by entering control commands via user interface 108 to stop operation of pump 102. After the user has refilled or replaced product reservoir 103, the user may manually re-start pump 102 and dispensing site 105, or may enter control commands via user interface 108 to cause controller 104 to send control signals via connection 118 to re-start pump 102. Controller 104 may further re-set, or clear, alerts 106 at the appropriate time (for example, after being manually cleared by a user, after product reservoir 103 has been refilled or system 100A is restarted).

Alternatively, controller 104 may automatically stop pump 102 and/or dispensing site 105 when an out-of-product event is detected. In this embodiment, controller 104 may send control signals to pump 102 across connections 118 to temporarily stop operation of the corresponding components without user intervention. Controller 104 may then re-start pump 102 and/or dispensing site 105 after receiving input from the user or otherwise that product reservoir 103 has been refilled or replaced. Controller 104 may then send further control signals across connections 118 to restart pump 102. Alternatively, acoustic sensor 200 or controller 104 may initiate an automatic refill cycle after which the out-of-product alert would be cleared and the system started again.

Acoustic sensor 200 or system controller 104 may also generate a visual indicator or message that indicates presence of fluid within input tubing 120. For example, a light of one color, such as green, may be used to indicate that product reservoir 103 has product remaining, while a light of another color, such as red or blinking, may be used to indicate that product reservoir 103 is substantially empty and needs to be refilled or replaced. A product full/empty icon or other message may also be displayed on user interface 108.

Figure 1B:
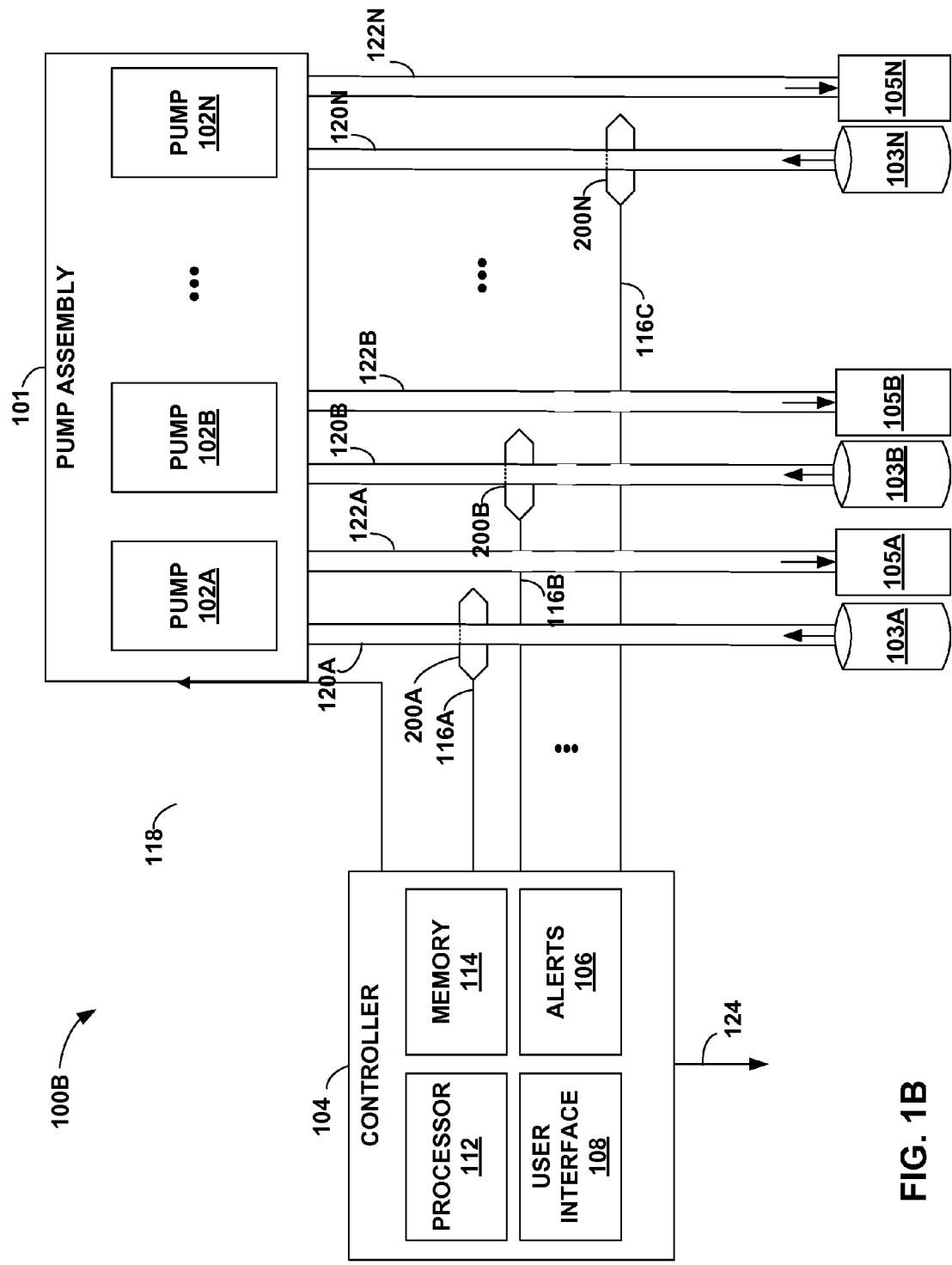
FIG. 1B is a block diagram illustrating another example of a fluid dispensing system utilizing multiple acoustic sensors, each of which detects presence and/or absence of a different product to be dispensed.

FIG. 1B is a diagram illustrating another example fluid dispensing system 100B. Fluid dispensing system 100B dispenses multiple products. To that end, fluid dispensing system 100B includes multiple product channels (A-N), each having associated product reservoirs 103A-103N, dispensing sites 105A-105N and pumps 102A-102N. System 100B also includes a system controller 104. Pumps 102A-102N are included in pump assembly 101. Pumps 102A-102N draw in fluid from a respective product reservoir 103A-103N through an input tubing 120A-120N, and supply fluid to one of dispensing sites 105A-105N through output tubing 122A-122N. Each product reservoir 103A-103N may contain any of a multitude of different types of products having varying color, transparency and/or turbidity. Acoustic sensors 200A-200N detect presence and/or absence of the product dispensed in the respective dispensing channel.

Although the example fluid dispensing system 100B shown in FIG. 1B shows each dispensing channel as having its own dedicated product reservoir 103, input tubing 120, output tubing 122, pump 102, dispensing site 105 and acoustic sensor 200, it shall be understood that there need not be a one to one correspondence for each dispensing channel. For example, sensors 200A-200N may be implemented in a single unit through which the input tubing for each dispensing channel is routed. Alternatively, various combinations of one channel per sensor or two or more channels per sensors may also be used and the invention is not limited in this respect. Also each product may be routed to one or more of dispensing sites 105A-105N, depending upon where they are to be used.

Likewise, the example pump assembly 101 of FIG. 1B includes multiple pumps 102A-102N, one for each dispensed product. It shall be understood, however, that there need not be a one to one correspondence between pumps 102A-102N and the dispensing channels. For example, some dispensed products may share one or more pumps, which are switched from one dispensed product to another under control of system controller 104. The pump or pumps 102A-102N provide fluid to the appropriate dispensing site 105 from one of product reservoirs 103A-103B.

It shall also be understood that any of sensors 200A-200N may also be positioned to detect presence and/or absence of product within output tubing 122A-122N rather than input tubing 120A-120N as shown in FIG. 1B, and that the location of sensors 200A-200N may be more a matter of convenience than of system performance.

Controller 104 is coupled to pump assembly 101 via connection 121. Through connection 121, controller 104 is able to communicate with pump assembly 101 and effectively communicate and/or control operation of each individual pump 102 (e.g., to temporarily stop or start operation, as described previously in reference to FIG. 1A). Depending upon the application, controller 104 may also communicate with one or more dispensing sites 105A-105N.

Each acoustic sensor 200A-200N detects presence and/or absence of fluid within the corresponding fluid delivery medium, in this case input tubing 120A-120N. Controller 104 is coupled to each acoustic sensor 200A-200N via a corresponding connection 116A-116N. Controller 104 monitors the signals received from each acoustic sensor 200A-200N, and may respond as described above to any detected out-of-product events. For example, controller 104 may generate a visual or audible alert 106 or display a message on user interface 108 if one or more of the sensors 200A-200N has detected an out-of-product event. The visual or audible alert 106 and/or message displayed on user interface 108 and/or message sent via pager, e-mail, cell phone, text message, or other form of electronic communication, etc. would indicate which of product reservoirs 103A-103N is empty, thus informing a user which product reservoir needs to be filled or replaced. Controller 104 may also automatically temporarily stop and then re-start the pump 102A-102N corresponding to the empty product reservoir 103A-103N and/or may initiate an automatic refill cycle of the empty product reservoir as described above.

Although in FIG. 1B each acoustic sensor 200A-200N is shown with a dedicated connection 116 to controller 104, it shall be understood that sensors 200A-200N may be connected to communicate with controller 104 in any of several different ways. For example, sensors 200A-200N may be connected to controller 104 serially or in a daisy-chain fashion. In this example, controller 104 is coupled directly to a first acoustic sensor 200A via connection 116 and each subsequent acoustic sensor 200B-200N is coupled the next sensor, etc. A communication protocol to identify and communicate separately with each acoustic sensor 200A-200N may also be used. It shall be understood, however, that the invention is not limited with respect to the particular architecture or communication protocol by which sensors 200A-200N are connected with and communicate with controller 104, and that the system may be set up in many different ways known to those of skill in the art.

Figure 2:
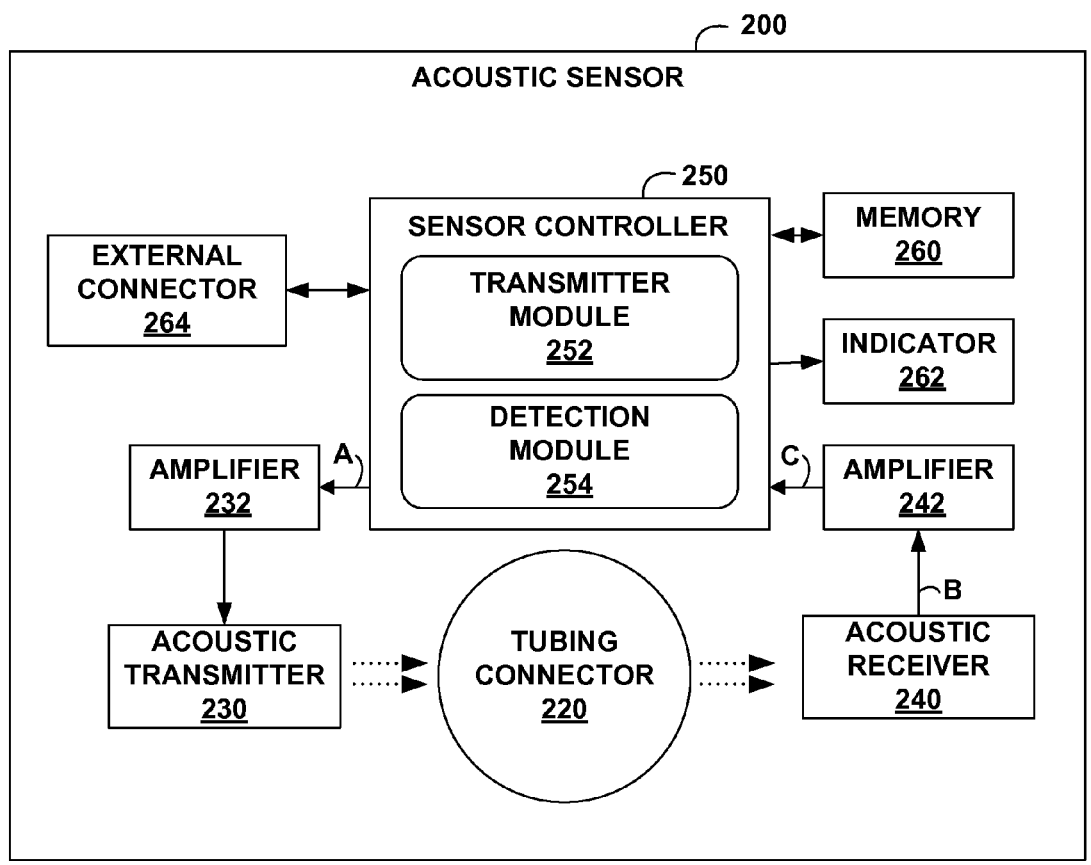
FIG. 2 is a block diagram illustrating an example of an acoustic sensor that detects presence or absence of a product within a fluid delivery medium.

FIG. 2 is a block diagram illustrating an example embodiment of an acoustic sensor 200 that detects presence and/or absence of a fluid within a fluid delivery medium. Acoustic sensor 200 may include, for example, a controller 250, a memory 260, an acoustic transmitter 230, an acoustic receiver 240 and a tubing connector 220. Acoustic sensor 200 may also include at least one optional external connector 264 and/or an optional indicator 262. The components of acoustic sensor 200 may be implemented on a single printed circuit board (PCB) or may be implemented using two or more PCB boards. Acoustic sensor 200 may communicate with external devices, such as controller 104 or other acoustic sensors via external connector 264.

Memory 260 stores software and data used or generated by controller 250. As will be discussed in more detail below, memory may store baseline detection values produced by acoustic receiver 240 and processed by controller 250. During operation of acoustic sensor 200, controller 250 may control indicator 262 based upon information received from acoustic receiver 240. For example, upon detection of an out-of-product event, controller 250 may cause indicator 262 to generate a visual or audible out-of-product alert. Controller 250 may additionally send an out-of-product message to an external device, such as controller 104, via connector 264.

In this example, acoustic transmitter 230 and acoustic receiver 240 are placed approximately opposite each other on either side of the fluid delivery medium positioned within tubing connector 220. In some embodiments, acoustic transmitter 230 and acoustic receiver 240 may be placed in contact with fluid delivery medium 120. Fluid delivery medium 120 may be slightly compressed between acoustic transmitter 230 and acoustic receiver 240, or the system may be otherwise configured to achieve a close fit between transmitter 230, receiver 240 and fluid delivery medium 120.

In this example, sensor controller 250 is programmed, via transmitter module 252, to generate an excitation signal (point A in FIG. 2). The excitation signal may be amplified by an excitation signal amplifier 232 to produce the necessary power to excite acoustic transmitter 230. In response to the excitation signal, acoustic transmitter 240 emits an acoustic interrogation signal into the fluid delivery medium positioned within tubing connector 220. Acoustic receiver 240 receives the interrogation signal transmitted through the fluid delivery medium and converts the received acoustic signal to a corresponding electrical output signal (point B in FIG. 2). The output signal may be amplified by an amplifier 242 (point C in FIG. 2). The output signal is provided to sensor controller 250 and detection module 254, which determines presence and/or absence of fluid within the fluid delivery medium based on the phase shift between the excitation signal and the output signal.

In some example embodiments, the frequency of the excitation signal, and thus the frequency of the acoustic interrogation signal generated by acoustic transmitter 230, is chosen such that the wavelength of the acoustic interrogation signal is on the same order as the diameter of the fluid delivery medium. For example, an appropriate interrogation frequency may be one that is close to resonance for a standing wave of the particular acoustic configuration. Under these conditions, the difference in the amplitude of the received acoustic signals for fluid presence as compared to fluid absence is minimal. However, as the acoustic interrogation signals emitted by acoustic transmitter 230 propagate through the fluid delivery medium, their phase is affected differently depending upon whether the fluid delivery medium contains mostly fluid, a combination of fluid and air (e.g., bubbles in a fluid) or mostly air. Depending upon the interrogation frequency and closeness to resonance for the particular acoustic configuration, the phase shift of the received signals for fluid presence as compared to fluid absence may be in the range from 90 degrees to 270 degrees. The phase shift between received signals for fluid presence as compared to received signals for fluid absence can be measured in different ways known to those skilled in art. An excitation signal can be shifted in phase using known means to have a zero phase shift relative to received signal when fluid is present. For example, for a 0.5 inch (1.27 cm) tubing internal diameter (ID), an example acoustic frequency may be approximately 16 kHz, which corresponds to a 7.7 cm wavelength in water and a 1.72 cm wavelength in air and a corresponding phase shift of 164 degrees.

In general, as the tubing diameter increases, the excitation frequency may (but need not necessarily) be decreased. In some examples, the excitation frequency may be chosen such that a wavelength in air of the excitation signal is between 0.3 and 1 times the diameter of the fluid delivery medium. In another example, the approximate relationship between the tubing diameter and excitation frequency is such that the tubing diameter on the same order as V/2T, where V is the speed of the sound in the air and T is the period of the excitation signal. In other words, the distance between the acoustic transmitter and acoustic receiver may be on the same order as V/2T. For simplicity, the same excitation frequency may be used for multiple tubing diameters. For example, the same excitation frequency 16 kHz may be used for ⅜ inch and ½ inch diameter tubing, but the frequency may be changed, for example, decreased to 8 kHz, for 1 inch diameter tubing. In other examples, a different excitation frequency may be used with each different tubing diameter. In general, the acoustic sensors may operate in the low frequency range of 10 kilohertz to 40 kilohertz. Example tubing diameters and example corresponding excitation frequencies are described in Table 1 below. The excitation frequencies listed in Table 1 result in a phase shift of the received signals for fluid presence as compared to fluid absence of approximately 160 degrees.

TABLE 1

| Tubing diameter | Excitation Frequency |
|---|---|
| 20 mm | 10 kHz |
| 15 mm | 13.3 kHz |
| 5 mm | 40 kHz |
| ⅜ inch | 21 kHz |
| ½ inch (12.7 mm) | 15.8 kHz |
| 1 inch (25.4 mm) | 7.9 kHz |

Sensor controller 250 controls operation of acoustic transmitter 230 and receives information concerning the received acoustic signal from acoustic receiver 240. Controller 250 executes a transmitter module 252 that controls acoustic transmitter 230, and includes a detection module 254 that processes signals received from acoustic receiver 240. If detection module 254 detects an out-of-product event, sensor controller 250 may activate an out-of-product indicator 262 and/or send a corresponding out-of-product message to an external device via connector 264. In some examples, detection module 254 may also activate indicator 262 and/or send a corresponding output message if it confirms presence of fluid within the tubing.

Detection module 254 within sensor controller 250 processes the outputs received from acoustic receiver 240 to detect presence and/or absence of fluid within the fluid delivery medium. Detection module 254 detects presence and/or absence of fluid within the fluid delivery medium based on the phase shift between the excitation signal and the received acoustic signal. Detection module 254 measures a phase shift between the excitation signal and the acoustic output signal. The phase shift may be determined, for example, by the following equation:

$$\Delta\phi(t)=\phi(t)_{ex}-\phi(t)_{rec}, \text{ where}$$

$\phi(t)_{ex}$ is the phase of the excitation signal
$\phi(t)_{rec}$ is the phase of the acoustic output signal, and
$\Delta\phi(t)$ is the phase shift between the excitation signal and the acoustic output signal.

To determine presence or absence of fluid, sensor controller 250 may compare the phase shift with one or more predetermined out-of-product threshold criteria. If the predetermined out-of-product threshold criteria is/are satisfied, sensor controller 250 may detect an out-of-product event. For example, if the measured phase shift is greater than (or less than, depending upon the threshold criteria) the predetermined out-of-product threshold criteria, sensor controller 250 may detect an out-of-product event. In another example, sensor controller 250 may compare the phase shift with predetermined lower and upper threshold criteria as follows:

$$\Delta\phi(t)_{thresh1} < |\Delta\phi(t)| < \Delta\phi(t)_{thresh2}, \text{ where}$$

$\Delta\phi(t)_{thresh1}$ is a predetermined lower threshold criteria, and
$\Delta\phi(t)_{thresh2}$ is a predetermined upper threshold criteria.

If the threshold criteria is satisfied, namely, when the phase shift is between the predetermined lower and upper threshold criteria, sensor controller 250 may detect an out-of-product event. On the other hand, if the threshold criteria is not satisfied, sensor controller 250 may determine that product is present within the fluid delivery medium.

For a given tubing diameter, a predetermined level of phase shift between the excitation signal and the acoustic output signal when fluid is present may be set by varying the excitation signal frequency. For example, the excitation signal frequency may be chosen such the phase shift between the excitation signal and the acoustic output signal when fluid is present is between 25 degrees and 60 degrees. The lowest frequency that provides such shift may be used.

Including an initial predetermined level of phase shift when fluid is present may help to ensure detection of true out-of-product events and may also help to reduce or minimize false positives. An example of a suitable predetermined lower threshold criteria (for a phase shift between 25 degrees and 60 degrees when fluid is present) may be approximately 90 degrees, and an example of a suitable predetermined upper threshold criteria under these conditions may be approximately 180 degrees. For example, when sensor controller 250 determines that the phase shift between the excitation signal and the acoustic output signal is between 90 and 180 degrees, sensor controller 250 may detect an out-of-product event. Such threshold criteria may help provide accurate detection of out-of-product events because the detected voltage of the acoustic output signal for an out-of-product event at such phase shifts will have a polarity opposite to that of the excitation signal. Initializing the system to include a predetermined phase shift when fluid is present permits usage of out-of-product threshold criteria of between 90 and 180 degrees, thus increasing sensor accuracy. Direct measurements of phase shift between the excitation signal and the acoustic output signal may allow use of the lowest frequencies and increase sensor robustness and stability. The out-of-product threshold criteria may be predetermined such that insignificant phase differences caused by occasional or accidental bubbles are not taken in account.

Figure 3:
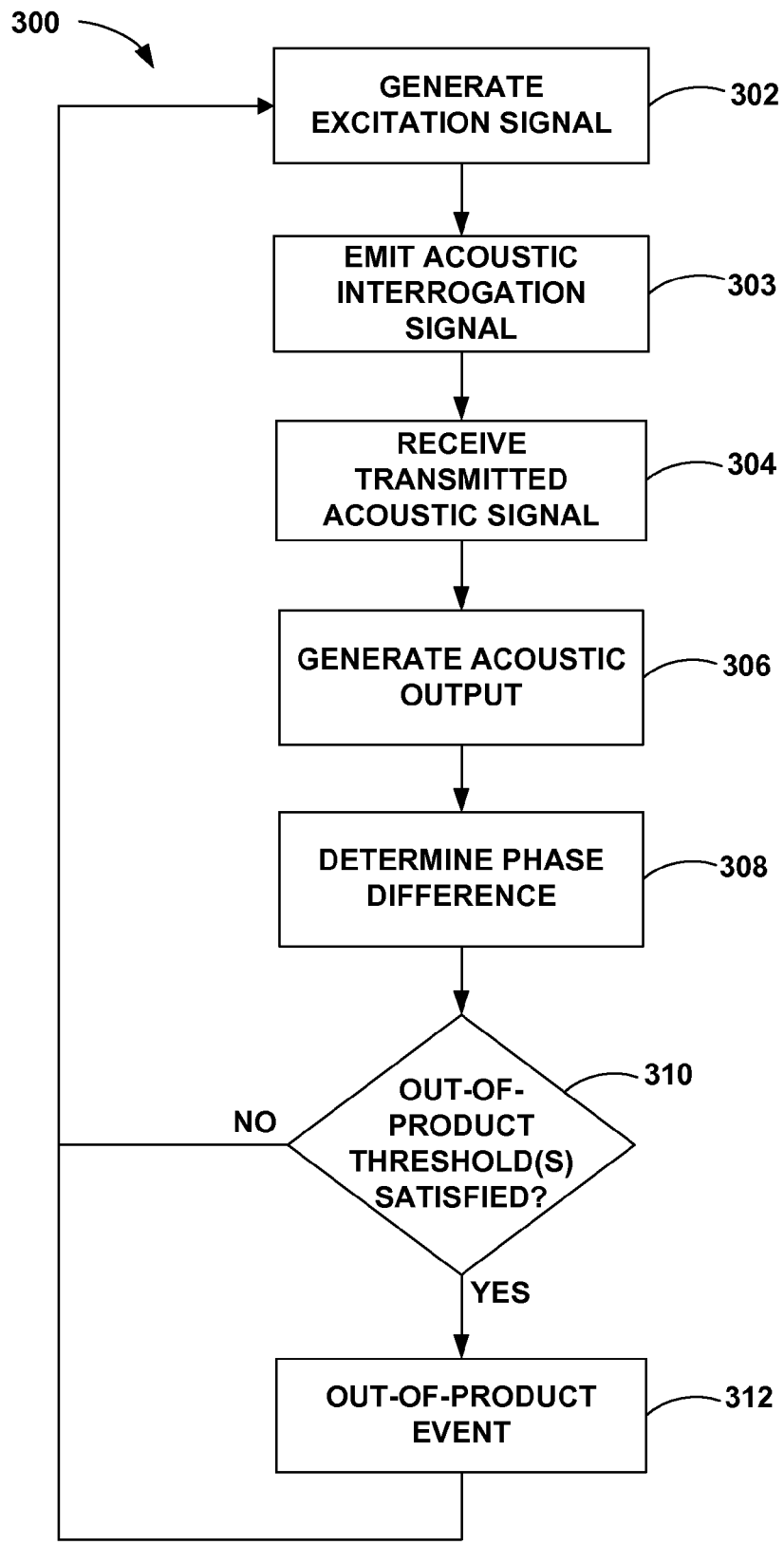
FIG. 3 is a flow chart illustrating operation of an example acoustic sensor.

FIG. 3 is a flow diagram illustrating an example process (300) by which acoustic sensor 200 determines presence and/or absence of fluid. Sensor controller 250 generates the excitation signal (302). The excitation signal may be amplified if necessary to generate enough power to excite acoustic transmitter 230. In response to the excitation signal, acoustic transmitter 230 emits the acoustic interrogation signal into the fluid delivery medium (or other medium) in which presence or absence of product is to be determined (303).

Acoustic receiver 240 receives the acoustic interrogation signal that is transmitted through the fluid delivery medium (304) and generates a corresponding acoustic signal output (306). The acoustic signal output may be amplified before being sent to sensor controller 250. Detection module 254 within sensor controller 250 determines the phase shift between the acoustic signal output and the excitation signal (308). Detection module 254 compares this phase shift with the predetermined out-of-product threshold criteria to detect presence and/or absence of fluid within the fluid delivery medium. If the out-of-product threshold is satisfied (310), detection module 254 (and thus sensor controller 250) detects an out-of-product event (312).

In some example embodiments acoustic sensor 200 operates in a continuous mode; that is, acoustic sensor continuously monitors for presence and/or absence of fluid within the fluid delivery medium. In continuous mode, acoustic transmitter 230 continuously emits an interrogation signal and acoustic receiver continuously receives the transmitted interrogation signal transmitted through the fluid-delivery medium. In other example embodiments, acoustic sensor 200 may monitor for presence and/or absence of fluid within the fluid delivery medium at predetermined intervals or at predetermined times of day. It shall be understood that acoustic sensor 200 may monitor for presence and/or absence of fluid either continuously or discretely, and that the invention is not limited in this respect.

Figure 4:
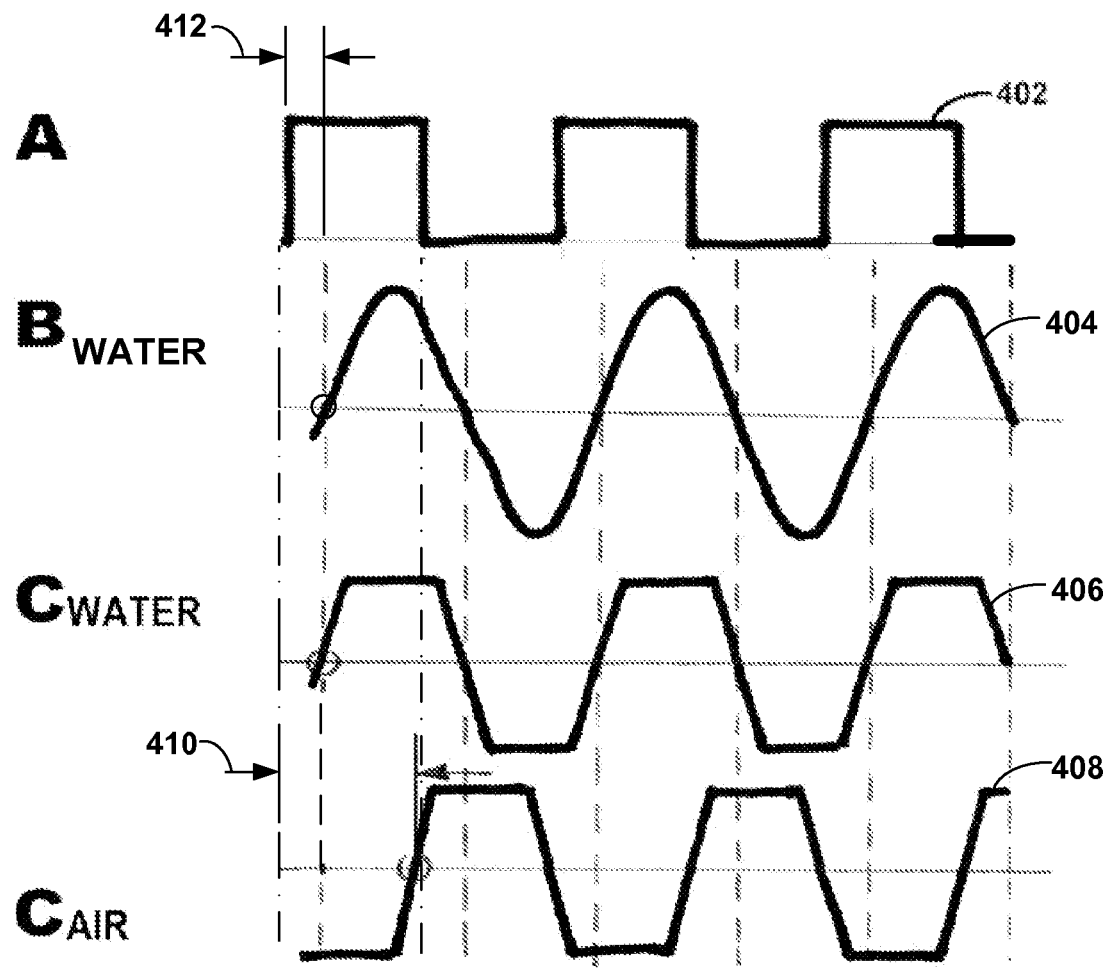
FIG. 4 are graphs illustrating example waveforms that may be generated by various components of an acoustic sensor.

FIG. 4 are graphs illustrating example waveforms that may be generated by various components of acoustic sensor 200. Waveform 402, labeled "A" represents an example excitation signal generated by sensor controller 250 (point A in FIG. 2). Transmitter module 252 is programmed to cause controller 250 to generate periodic square wave pulses such as those illustrated in FIG. 4 as waveform 402. Waveform 404, labeled $B_{WATER}$, represents an example acoustic output signal (a sinusoidal waveform) generated by acoustic receiver 240 with fluid present in the fluid delivery medium (point B in FIG. 2). In this example, because of resonance conditions, acoustic receiver 240 may generally pick out the first harmonic of the initial square wave excitation signal. In the example of FIG. 4, the frequency of the excitation signal was chosen such that the phase shift 412 between the excitation signal and the acoustic output signal when fluid is present, $B_{WATER}$, is between 25 degrees and 60 degrees.

Waveform 406, labeled $C_{WATER}$, represents an example amplified acoustic output signal generated by output amplifier 242 with water/fluid present in the fluid delivery medium (point C in FIG. 2). Output amplifier 242 is, in this example, an amplitude limiting amplifier having a gain large enough to generate saturated trapezoidal pulses that approximate a square-wave shape, such as those illustrated by waveform 406. Waveform 406 is substantially in phase with waveform 404 when fluid is present.

Waveform 408, labeled $C_{AIR}$, represents an example amplified acoustic output signal generated by output amplifier 242 with air present in the fluid delivery medium (point C in FIG. 2). The phase shift between the excitation signal 402 and the acoustic output signal 408 with air present is represented by reference numeral 410. For an initial phase shift 412 between 25 and 60 degrees, the phase shift 410 would be between 90 degrees and 180 degrees. In the example shown in FIG. 4, the phase shift is approximately 160 degrees. When the phase difference satisfies the predetermined out-of-product threshold criteria, acoustic sensor 200 detects an out-of-product event, and may generate an out-of-product message or alert as discussed above.

To determine the phase shift between the excitation signal and the acoustic output signal, sensor controller 250 may use a software or hardware implemented phase sensitive detector. As one example, the phase sensitive detector may be a lock-in amplifier. The output of a lock-in amplifier is essentially a DC signal that is proportional to the phase difference between a reference signal (in this case the excitation signal) and an input signal (in the case the acoustic output signal).

To implement a lock-in amplifier in software, detection module 254 of sensor controller 250 may include a multiplier module and a low pass filter module. The multiplier module takes a digital representation of the input signal (the acoustic output signal "B" from acoustic receiver 240 amplified by amplifier 242 "C", if necessary) and a digital representation of the reference signal (the excitation signal "A" generated by sensor controller 250) and multiplies them together. Because the excitation signal and the acoustic output are of the same frequency, the result is a DC output which is proportional to the amplitude of the input signal and the cosine of the phase difference between the signals. This DC output is then filtered by a low pass filter centered around the frequency of the excitation signal. The DC output is then compared with the predetermined threshold criteria to determine presence and/or absence of fluid and thus to detect an out-of-product event.

In another example, a lock-in amplifier may be implemented using discrete components as discussed below with respect to FIG. 6. Although the present specification has described using software or hardware implementations of a phase sensitive detector/lock-in amplifier principles for determining the phase shift between the excitation signal the acoustic output signal, it shall be understood that this is but one example and that other methods known to those of skill in the art now or in the future may also be used to determine the phase difference, and that the invention is not limited in this respect.

Figure 5:
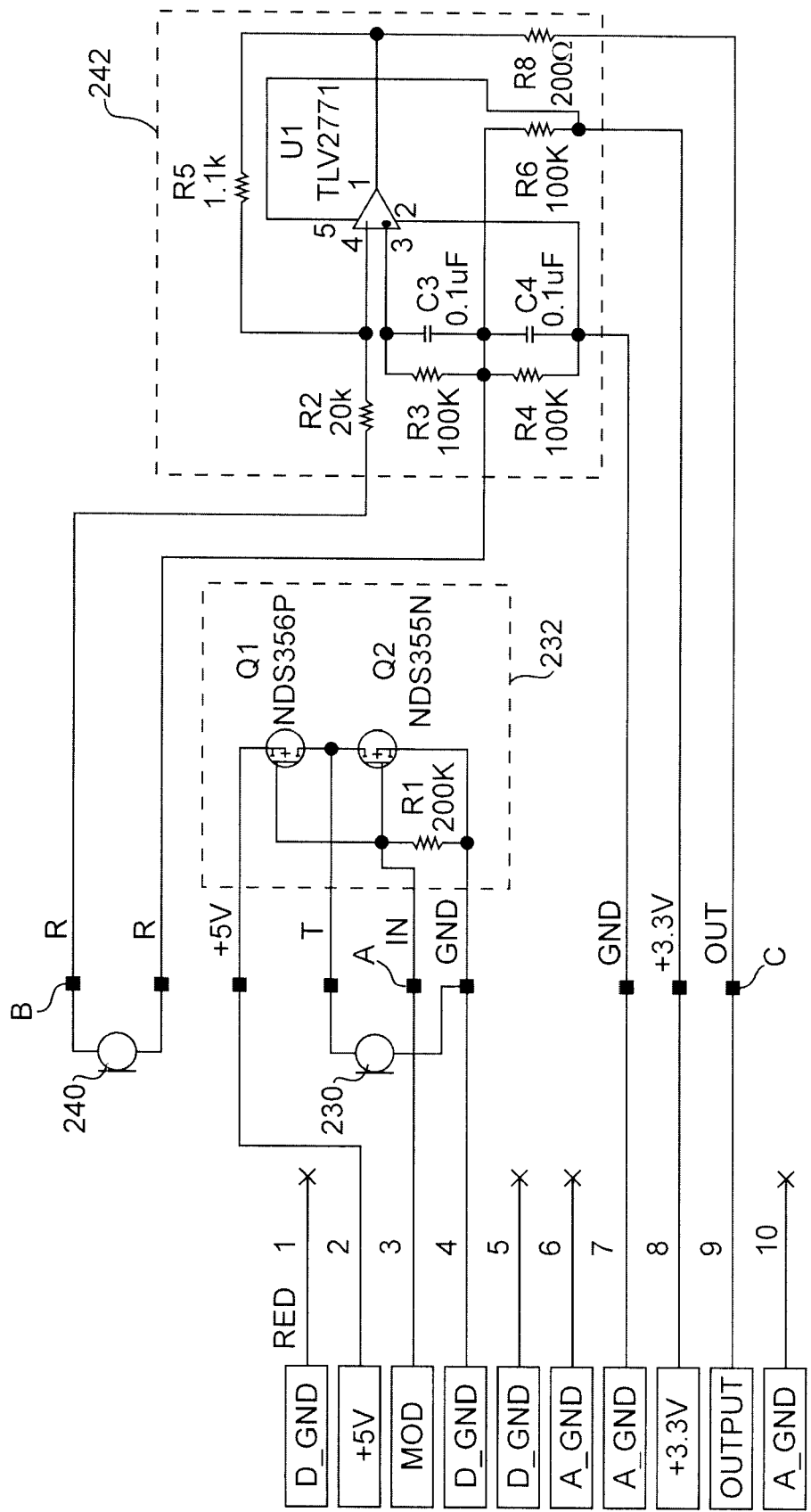
FIG. 5 is an electrical schematic diagram illustrating portions of an example acoustic sensor.

FIG. 5 is a schematic diagram illustrating portions of an example acoustic sensor 200. Specifically, FIG. 5 illustrates an example acoustic transmitter 230, an example acoustic receiver 240, an example excitation signal amplifier 232 and an example received acoustic signal amplifier 242 of an acoustic sensor 200 that detects presence and/or absence of a fluid. Although particular component values, part numbers, circuit design, configuration and layout are shown in FIG. 5, it shall be understood that the particular implementation shown in FIG. 5 is exemplary only, and that the invention is not limited in these respects. Those of skill in the art will readily appreciate that many other possible circuit designs, configurations, layouts, component values, part numbers, etc. may be substituted for the specific implementation shown in FIG. 5, and that many other embodiments are possible without departing from the spirit or scope of the present invention.

In the example shown in FIG. 5, the excitation signal (MOD) is received by amplifier 232 at the connector labeled "A" in FIG. 5 (which corresponds with line A in FIG. 2). In this example, amplifier 232 includes transistors Q1 and Q2 and resistor R1. The excitation signal is fed to transistors Q1 and Q2, thus switching Q1 and Q2 alternately on and off at the desired frequency. The amplified excitation signal excites acoustic transmitter 230 which then emits the acoustic interrogation signal at the desired frequency. The interrogation signal travels through the fluid delivery medium and the contents thereof, and the phase of the interrogation signal may be affected depending upon the relative amount of fluid and/or air within the fluid delivery medium. Acoustic receiver 240 receives the transmitted interrogation signal and generates a corresponding output signal (at connector "B" in FIG. 5, which corresponds to line B in FIG. 2), which is amplified by output amplifier 242. In this example, output amplifier 242 includes operational amplifier U1 and associated resistors R2, R3, R4, R5, R6 and R8, and capacitors C3 and C4. The resulting acoustic output signal (OUTPUT) is sent back to sensor controller 250 for analysis (at connector "C" in FIG. 5 which corresponds to line C in FIG. 2).

Figure 6:
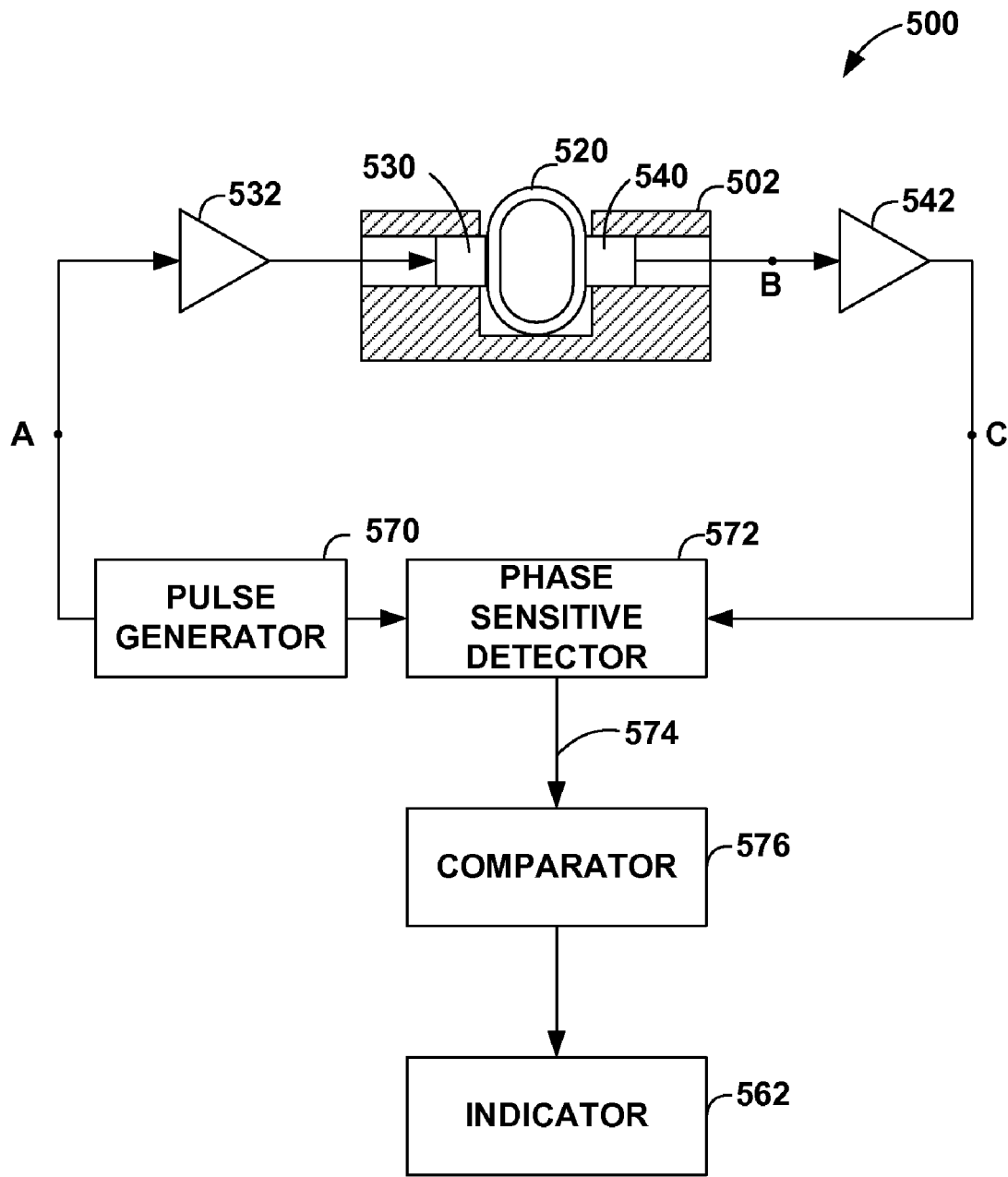
FIG. 6 is a block diagram illustrating another example embodiment of an acoustic sensor.

FIG. 6 is a block diagram illustrating another example embodiment of an acoustic sensor 500. Acoustic sensor 500 operates using principles similar to those discussed above with respect to acoustic sensor 200 (FIGS. 2-5). Acoustic sensor 500 uses discrete components rather than software to determine whether fluid is present or absent in a fluid delivery medium 520. Acoustic sensor 500 includes a pulse generator 570 that generates an excitation signal (line A) having the desired frequency and an amplifier 532 that amplifies the excitation signal to a level sufficient to excite acoustic transmitter 530. Acoustic transmitter emits a corresponding acoustic interrogation signal into fluid delivery medium 520. An acoustic receiver 540 receives the acoustic interrogation signals transmitted through fluid delivery medium 520 and transforms the received acoustic signals to electrical oscillations (line B). An amplitude-limiting amplifier 542 includes a gain large enough to produce an output of saturated trapezoidal pulses that approximate a square-wave shape. A phase-sensitive detector 572 receives the output signal of amplifier 542 and the excitation signal from pulse generator 530. Phase sensitive detector 572 may be implemented using a lock-in multiplier that mixes the output signal of amplifier 542 with pulses of oscillator 570. The output signal of phase sensitive detector 572 produced on line 574 is a DC voltage. The amplitude and polarity of the DC output voltage depends on the phase difference between the excitation signal (on line A) and the acoustic output signal (line C). A comparator 578 compares the DC output voltage with a predetermined out-of-product threshold criteria. If the threshold criteria is satisfied, an out-of-product indicator 562 may be activated. Alternatively or in addition, an out of product message may be sent to an external device, such as controller 104 (FIG. 1).

Pulse generator 570 may be a square pulse oscillator that generates square wave pulses similar to waveform 402 as illustrated in FIG. 4. Amplifier 532 may be an amplitude limiting amplifier that includes a gain large enough to produce an output of saturated trapezoidal pulses approximating a square-wave shape, such as waveform 406 as illustrated in FIG. 4. Acoustic transmitter 530 may be implemented using a piezo-electric transducer that generates the acoustic interrogation signal in response to the excitation signal. Acoustic receiver 540 may be implemented using a piezo-electric transducer that receives the acoustic waveform transmitted through the fluid delivery medium and converts it to an electrical acoustic output signal waveform. Acoustic transmitter 530 and acoustic receiver 540 may also be implemented using other transmitters and/or receivers known to those of skill in the art, such as electromagnetic acoustic transducers or magnetostrictive transducers, and it shall be understood that the invention is not limited in this respect.

The acoustic sensors described herein may provide several advantages. For example, the acoustic sensors are applicable to tubing having a wide variety of different tubing diameters. When the tubing size is changed, the acoustic excitation frequency may be changed.

As another example, the acoustic sensors described herein may be effective in those applications in which non-transparent, opaque or braided/mesh tubing is installed. In such situations, the effectiveness of optical sensing techniques may be reduced. The acoustic sensors may also be effective in applications utilizing larger tubing diameters. In a large tubing diameter application, attenuation experienced as optical signals travel over the larger tubing distance may impact system performance and/or accuracy. In the acoustic sensors described herein, attenuation experienced by the acoustic interrogation signals may be less significant, which may result in greater accuracy in fluid absence detection.

As another example, the acoustic sensors described herein may work with many different fluid products, including those having different viscosities, color, turbidity, etc.

As another example, the response time of the acoustic sensors described herein is approximately 10-100 milliseconds. This is sufficiently fast for an out-of-product sensor application. The non-critical response time allows lower frequencies on the order of the tubing diameter to be used.

As another example, because the acoustic interrogation signal is in the ultrasound range, and because the interrogation signal travels within the tubing and not outside of the device, the acoustic sensors do not produce loud, harmful or disturbing sounds which may adversely affect or bother humans who may be in the vicinity of the device.

Various embodiments of the invention have been described. These and other embodiments are within the scope of the following claims.

The invention claimed is:

1. A method comprising:
generating an excitation signal having an excitation frequency;
emitting, in response to the excitation signal, an acoustic interrogation signal having the excitation frequency into a fluid delivery medium in which presence or absence of a fluid is to be determined, the excitation frequency chosen such that an initial phase shift between an acoustic signal output and the excitation signal is between 25 degrees and 60 degrees when fluid is present;
receiving the acoustic interrogation signal transmitted through the fluid delivery medium and generating therefrom the acoustic signal output;
determining a phase shift between the acoustic signal output and the excitation signal; and
determining presence or absence of the fluid within the fluid delivery medium based on the phase shift.

2. The method of claim 1, further comprising comparing the phase shift with at least one predetermined threshold criteria to determine presence of absence of fluid within the fluid delivery medium.

3. The method of claim 2, further comprising detecting an out-of-product event when the at least one predetermined threshold criteria is satisfied.

4. The method of claim 1, wherein determining the phase shift comprises multiplying the excitation signal and the acoustic signal output and obtaining therefrom a DC output signal indicative of the phase shift between the acoustic signal output and the excitation signal.

5. The method of claim 1, wherein determining presence or absence of the fluid within the fluid delivery medium comprises comparing the phase shift to a predetermined lower threshold criteria and a predetermined upper threshold criteria.

6. The method of claim 5, further comprising detecting an out-of-product event when the phase shift is between the predetermined lower threshold criteria and the predetermined upper threshold criteria.

7. The method of claim 1, further comprising generating an out-of-product alert when absence of fluid in the fluid delivery medium is determined.

8. The method of claim 7, wherein generating the out-of-product alert comprises generating at least one of a message to an external device, a visible indicator, or an audible indicator.

9. The method of claim 7, wherein generating an out-of-product alert comprises generating at least one of a text message, e-mail, cell phone message, page or other electronic communication.

10. The method of claim 1, further comprising detecting an out-of-product event when the phase shift is between 90 and 180 degrees.

11. A sensor, comprising:
an acoustic transmitter, driven by an excitation signal having an excitation frequency, that emits an acoustic interrogation signal having the excitation frequency into a fluid delivery medium in which presence or absence of a fluid is to be determined, the excitation frequency chosen such that an initial phase shift between an acoustic signal output and the excitation signal is between 25 degrees and 60 degrees when fluid is present in the fluid delivery medium;
an acoustic detector that generates an acoustic signal output having the excitation frequency based on detection of the acoustic interrogation signal transmitted through the fluid delivery medium; and
a controller that calculates a phase shift between the acoustic signal output and the excitation signal, compares the phase shift with at least one predetermined threshold criteria and determines presence or absence of the fluid within the fluid delivery medium based on the phase shift.

12. The sensor of claim 11, wherein the controller further includes a transmitter module that controls generation of the excitation signal.

13. The sensor of claim 12, wherein the controller detects an out-of-product event when the phase shift is between the predetermined lower threshold and the predetermined upper threshold.

14. The sensor of claim 11, wherein the controller further includes a detection module that multiplies the excitation signal and the acoustic signal output to obtain a DC output signal indicative of the phase shift between the acoustic signal output and the excitation signal.

15. The sensor of claim 11, wherein the controller compares the phase shift to a predetermined lower threshold and a predetermined upper threshold.

16. The sensor of claim 11, wherein the controller further generates an out-of-product alert when absence of fluid in the fluid delivery medium is determined.

17. The sensor of claim 16, wherein the out-of-product alert is at least one of a message to an external device, a visible indicator, or an audible indicator.

18. The sensor of claim 11, wherein the excitation frequency is between about 5 kilohertz and 40 kilohertz.

19. The sensor of claim 11, wherein the excitation frequency is chosen such that a wavelength in air of the excitation signal is between 0.3 and 1 times the diameter of the fluid delivery medium.

20. The sensor of claim 19, wherein the excitation frequency is chosen such that one half of the wavelength in air of the excitation signal is approximately equal to the diameter of the fluid delivery tubing.

21. The sensor of claim 11 wherein the controller further detects an out-of-product event when the phase shift is between 90 and 180 degrees.

22. A computer readable medium comprising instructions that cause a programmable processor to:
generate an excitation signal that excites emission of an acoustic interrogation signal into a fluid delivery medium in which presence or absence of a fluid is to be determined, the excitation frequency having a frequency such that an initial phase shift between an acoustic signal output and the excitation signal is between 25 degrees and 60 degrees when fluid is present in the fluid delivery medium;
receive the acoustic interrogation signal transmitted through the fluid delivery medium and generate therefrom an acoustic signal output;
determine a phase shift between the acoustic signal output and the excitation signal; and
determine presence or absence of the fluid within the fluid delivery medium based on the phase shift.

23. The computer readable medium of claim 22, further comprising instructions that cause a programmable processor to compare the phase shift with at least one predetermined threshold criteria.

24. The computer readable medium of claim 23, further comprising instructions that cause a programmable processor to detect an out-of-product event when the at least one predetermined threshold criteria is satisfied.

25. The computer readable medium of claim 22, further comprising instructions that cause a programmable processor to multiply the excitation signal and the acoustic signal output and obtaining therefrom a DC output signal indicative of the phase shift between the acoustic signal output and the excitation signal.

26. The computer readable medium of claim 22, further comprising instructions that cause a programmable processor to generate an out-of-product alert when absence of fluid in the fluid delivery medium is determined.

27. The computer readable medium of claim 22, further comprising instructions that cause a programmable processor to detect an out-of-product event when the phase shift is between 90 and 180 degrees.

* * * * *